US010513584B2

(12) United States Patent
Roy et al.

(10) Patent No.: US 10,513,584 B2
(45) Date of Patent: Dec. 24, 2019

(54) PLATINUM CATALYZED HYDROSILYLATION REACTIONS UTILIZING CYCLODIENE ADDITIVES

(71) Applicant: MOMENTIVE PERFORMANCE MATERIALS INC., Waterford, NY (US)

(72) Inventors: Aroop K. Roy, Mechanicville, NY (US); Julie L. Boyer, Columbia, MD (US)

(73) Assignee: MOMENTIVE PERFORMANCE MATERIALS INC., Waterford, NY (US)

(*) Notice: Subject to any disclaimer, the term of this patent is extended or adjusted under 35 U.S.C. 154(b) by 0 days.

(21) Appl. No.: 16/009,366

(22) Filed: Jun. 15, 2018

(65) Prior Publication Data
US 2018/0291154 A1    Oct. 11, 2018

Related U.S. Application Data

(63) Continuation of application No. 14/969,559, filed on Dec. 15, 2015, now Pat. No. 10,000,611, which is a continuation-in-part of application No. 14/737,930, filed on Jun. 12, 2015, now Pat. No. 9,434,749.

(60) Provisional application No. 62/106,347, filed on Jan. 22, 2015, provisional application No. 62/011,825, filed on Jun. 13, 2014.

(51) Int. Cl.
| | |
|---|---|
| *C08G 77/08* | (2006.01) |
| *C08G 77/00* | (2006.01) |
| *C09D 183/04* | (2006.01) |
| *C07F 7/18* | (2006.01) |
| *C07F 7/08* | (2006.01) |
| *C07F 7/12* | (2006.01) |
| *C07F 7/14* | (2006.01) |
| *C09D 143/04* | (2006.01) |

(52) U.S. Cl.
CPC .......... *C08G 77/08* (2013.01); *C07F 7/0829* (2013.01); *C07F 7/0879* (2013.01); *C07F 7/12* (2013.01); *C07F 7/14* (2013.01); *C07F 7/1804* (2013.01); *C07F 7/1876* (2013.01); *C08G 77/70* (2013.01); *C09D 143/04* (2013.01); *C09D 183/04* (2013.01)

(58) Field of Classification Search
None
See application file for complete search history.

(56) References Cited

U.S. PATENT DOCUMENTS

| | | |
|---|---|---|
| 3,159,601 A | 12/1964 | Ashby |
| 3,220,972 A | 11/1965 | Lamoreaux |
| 3,775,452 A | 11/1973 | Karstedt |
| 5,563,287 A | 10/1996 | Roy |
| 5,567,848 A | 10/1996 | Roy |
| 6,605,734 B2 | 8/2003 | Roy et al. |
| 2003/0109732 A1* | 6/2003 | Roy .......................... C07F 7/14 556/10 |
| 2006/0135689 A1 | 6/2006 | Fehn |

FOREIGN PATENT DOCUMENTS

| | | |
|---|---|---|
| EP | 0491509 | 6/1992 |
| EP | 0785202 | 7/1997 |
| EP | 1672031 A1 | 6/2006 |
| JP | 54076529 A | 6/1979 |
| JP | 54076530 A | 6/1979 |
| JP | H04-128292 | 4/1992 |
| WO | 03050130 | 6/2003 |
| WO | 2013000788 A1 | 1/2013 |
| WO | 2015192029 A1 | 12/2015 |

OTHER PUBLICATIONS

Roy et al., J. Amer. Chem. Soc. 2002, 124, 9510-9524. (Year: 2002).*
Junchang Zhou et al., "Preparation of long-chain alkyl silicone oil," Collected Papers of the 1st Guangdong Textile Auxiliary Industry Annual Conference, Feb. 16, 2009.
Chinese Patent Office, Notification of First Office Action for Patent Application No. 201580056414.9, dated May 7, 2019.
PCT International Search Report and Written Opinion for PCT/US2015/035594, dated Sep. 16, 2015, International Search Authority/European Patent Office, Netherlands.
Speier, et al., "The Addition of Silicon Hydrides to Olefinic Double Bonds. Part II. The Use of Group VIII Metal Catalysts" J. Am. Chem. Soc. 79, 974 (1957).
Lewis et al., "Platinum-Catalyzed Hydrosilylation of Alkynes" Organometallics, 1991, 10, 3750-3759.
Caseri et al., "Hydrosilylation Chemistry and Catalysis with cis-PcLC2(PhCH+CH2)2" Organometallics, 1988, 7, 1373-1380.
Downing, et al., "Diethyl Sulfide Stabilization of Platinum-Complex Catalysts for Hydrosilylation of Olefins." Catalysis Communications, Mar. 30, 2011, vol. 12, No. 12, pp. 1166-1169, Elsevier Science, Amsterdam, NL.
Sprenger, et al., "Stable Platinum(0) Catalysts for Catalytic Hydrosilylation of Styrene and Synthesis of [Pt (Ar-bian) ([eta]2-alkene)] Complexes." European Journal of Inorganic Chemistry, Oct. 1, 2003, vol. 2003, No. 20, pp. 3811-3819.

(Continued)

*Primary Examiner* — Clinton A Brooks
*Assistant Examiner* — Kofi Adzamli
(74) *Attorney, Agent, or Firm* — Joseph Waters; McDonald Hopkins LLC

(57) ABSTRACT

A process and composition for the hydrosilylation of an unsaturated compound comprising reacting (a) a silyl hydride with (b) an unsaturated compound in the presence of (c) a platinum compound and (d) a cyclodiene, with the proviso that when the unsaturated compound is a terminal alkyne, the silyl hydride is other than a halosilane. The process and composition optionally comprise an inhibitor (e). The process and composition may be employed to form a variety of hydrosilylation products.

17 Claims, 2 Drawing Sheets

(56) References Cited

OTHER PUBLICATIONS

Vekki, et al., "Spectral Study of the Catalytic Reaction of Hydrosiloxanes with Vinylsiloxanes." Russian Journal of Gemal Chemistry, 2004, vol. 74, No. 9, pp. 1321-1327.
Patent Cooperation Treaty (PCT), International Search Report and Written Opinion for Application PCT/US2015/065752 filed Dec. 15, 2015, dated Mar. 18, 2016, International Searching Authority, EP.
Roy et al., J. Amer. Soc. 2002, 124, 9510-9524.

* cited by examiner

PLATINUM CATALYZED HYDROSILYLATION REACTIONS UTILIZING CYCLODIENE ADDITIVES

CROSS-REFERENCE TO RELATED APPLICATIONS

The present application is a continuation of U.S. application Ser. No. 14/969,559 filed on Dec. 15, 2015, which (i) claims priority to and the benefit of U.S. Provisional Application No. 62/106,347 filed on Jan. 22, 2015, the entire disclosure of which is incorporated herein by reference in its entirety; and (ii) is a continuation-in-part of and claims priority to and the benefit of U.S. application Ser. No. 14/737,930 filed on Jun. 12, 2015, which claims priority to U.S. Provisional Application No. 62/011,825 filed on Jun. 13, 2014, the disclosures of which are incorporated herein by reference in their entireties.

FIELD OF THE INVENTION

The present invention relates generally to the use of cyclodiene additives for improved catalyst performance in platinum catalyzed hydrosilylation reactions.

BACKGROUND

Hydrosilylation chemistry, involving the reaction between a silylhydride and an unsaturated organic group, is the basis for synthetic routes to produce commercial silicone products such as silicone surfactants, silicone fluids and silanes as well as many addition cured products including sealants, elastomers, RTVs, adhesives, and silicone-based coatings. Conventionally, hydrosilylation reactions have been catalyzed by precious metal catalysts, such as platinum or rhodium metal complexes.

Various precious metal complex catalysts are known in the art. For example, U.S. Pat. No. 3,775,452 discloses a platinum complex containing unsaturated siloxanes as ligands. This type of catalyst is known as Karstedt's catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

Although these precious metal compounds and complexes are widely employed commercially as catalysts for hydrosilylation reactions including those employed in cure technology, they have several distinct disadvantages. One disadvantage of the current catalyst systems is the undesired color imparted to the final product. This yellow coloration or Pt precipitation in crude products often necessitates additional and costly purification steps. Another distinct disadvantage of the current systems is the progressive deactivation of the platinum catalysts during the course of the reaction which necessitates higher loadings of this costly metal. Yet another disadvantage encountered with Pt-catalyzed hydrosilylation of unsaturated and COH-terminated oligo- or polyethers is the undesired reaction of SiH with the alcohol OH, which produces SiOC linkages that waste SiH groups, leave unreacted C=C bonds, and can cause performance problems.

This need is particularly acute for release coating formulations for better performing catalysts at low Pt loadings, where perhaps the most stringent demand is placed on the catalyst for extremely fast cure at high line coating speeds and very short oven-dwell times (1-5 seconds), together with good bath life of the formulation. Yet, the formulation must essentially completely cure in seconds at elevated temperature to meet release performance requirements on a plethora of different paper and polymeric substrates. To accommodate these two opposing demands, two part formulations with high platinum loadings and high inhibitor loadings are typically employed in the industry. This current solution has several distinct disadvantages. High platinum catalyst loadings are required in addition curable systems to ensure rapid and complete cure at elevated temperature but this high loading of precious metal catalysts also imparts a significant catalyst cost to the formulation. High levels of inhibitors are employed to retard catalyst activity and to extend working life of the formulation at room temperature, but the inhibitors employed may not be rapidly decomplexed from the platinum center at elevated temperature and may slow the desired crosslinking reaction at elevated temperature.

Due to the high price of precious metals, catalysts derived from these platinum metals can constitute a significant proportion of the cost of silicone formulations. Over the last two decades, global demand for precious metals, including platinum, has sharply increased, driving prices several hundred folds higher, thereby precipitating the need for effective, yet lower catalyst loadings. There is a need in the silicone industry for platinum catalysts of improved stability. This improved stability would enable the lowering of Pt catalyst loadings and decreasing cycle time in reactors and improving yield for many hydrosilylations.

The use of pre-formed Pt-COD complexes (COD=1,5-cyclooctadiene) in hydrosilylation reactions has been previously reported, e.g., JP 54076530A, JP 54076529A, EP 472438, L. Lewis et al., Organometallics, 1991, 10, 3750-3759, and P. Pregosin et al., Organometallics, 1988, 7, 1373-1380. $PtCODCl_2$, $PtCODMe_2$, and $PtCODPh_2$ are commercially available and their use as catalysts for hydrosilylation has been known for many years. Roy et al. have reported the preparation of a series of $PtCOD(SiR_3)_2$ compounds from $PtCODCl_2$ (Roy, Aroop K.; Taylor, Richard B. J. Am Chem. Soc., 2012, 124, 9510-9524; and U.S. Pat. No. 6,605,734). Notably, the preparation of these $CODPtSi_2$ complexes strictly requires the use of at least three equivalents of COD per equivalent of Pt, even when prepared in situ for hydrosilylation catalysis, as COD is lost to both hydrogenation and isomerization (1,4-COD and 1,3-COD) reactions. This critical stoichiometry of COD/Pt is delineated both in the '734 patent and the JACS publication. Further, the use of only one COD per Pt led to no identifiable COD-Pt species, as reported in the JACS publication.

The use of pre-formed Pt (II) cyclooctadiene catalysts in addition cure reactions has been reported. The use of $PtCODPh_2$ has been reported for use in radiation cure systems in WO92/10529. Complexes with the general formula $PtCOD(alkynyl)_2$ and $Pt(COD)(ureylene)$ have been cited as catalysts in curable silicone rubber compositions, e.g., EP 0994159 and U.S. Pat. No. 7,511,110. These platinum II complexes, however, suffer from their poor solubility in organic solution and silicone formulations. Chlorinated solvents such as chloroform or dichloromethane are employed to dissolve the catalyst. In addition to health and environmental concerns posed by such chlorinated solvents, they are also highly volatile which poses formulation challenges.

The use of COD as an additive has been shown to reduce the amount of bis-silylated product in hydrosilylation of only alkynes with hydrochlorosilanes in U.S. Pat. No. 5,563,287. Other cyclodiene complexes of platinum are also known and commercially available, such as (norbornadiene)PtCl$_2$ and (dicyclopentadiene)PtCl$_2$, but again, these latter diene complexes are not known to provide any particular benefit over catalysts such as Speier's or Karstedt's.

There is a need in the silicone industry for platinum catalysts of improved stability as industry work-horse catalysts such as Speier's and Karstedt's are prone to partial deactivation via agglomeration, especially at elevated temperatures of use. Improved stability of the active catalyst would enable the lowering of Pt catalyst loadings. In addition to improved stability, catalysts that demonstrate rapid activation and high hydrosilylation activity at elevated temperature are especially sought. The present invention provides one solution to these needs.

SUMMARY

The present invention describes the use of cyclodiene additives to stabilize the platinum catalysts in hydrosilylation reactions. It has been found that cyclodiene additives are suitable for use in hydrosilylation reactions with a variety of unsaturated compounds and silanes. The stabilization can be achieved using a relatively low amount of cyclodiene additive. The use of cyclodiene additives may also allow for decreasing the platinum loading in hydrosilylation reactions. It has now been surprisingly found that cyclodiene additives, such as cyclooctadienes, can be used to stabilize platinum catalyst in hydrosilylation reactions. The stabilization can be observed, for example, by the ability to use lower platinum loadings in hydrosilylation reactions, improved color of the hydrosilylation products, and/or reduction of side reactions occurring during the process. The cyclodiene additives used may include 1,5-cyclooctadiene.

The present inventors have now unexpectedly discovered that the use of cyclodienes such as COD as additives, even at cyclodiene:Pt ratio as low as 1:1 and 2:1, and in conjunction with common Pt catalysts such as Speier's or Karstedt's helps stabilize active platinum catalysts in hydrosilylation reactions and leads to highly desirable catalysis improvements such as reduced level of Pt use, color reduction, reduction in by-products and shorter reaction time.

In one aspect, the present invention provides a process for producing a crosslinked product comprising reacting (a) a silyl hydride with (b) an alkenyl silicone in the presence of (c) a platinum compound, (d) a cyclodiene, and (e) optionally a cure inhibitor.

In another aspect, the present invention provides a composition comprising (a) a silyl hydride, (b) an alkenyl silicone compound, (c) a platinum compound, (d) a cyclodiene, and (e) optionally an inhibitor, where the cyclodiene (d) is a compound of the formula:

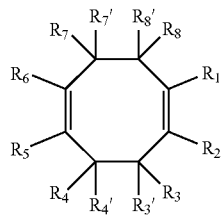

wherein R$^1$-R$^8$, R$^{3'}$, R$^{4'}$, R$^{7'}$, and R$^{8'}$ are independently hydrogen; an substituted or unsubstituted alkyl or aryl group optionally containing at least one heteroatom; an alkoxy; and a halogen radical; optionally R$^1$-R$^2$ and/or R$^5$-R$^6$ taken together may form a saturated or unsaturated ring structure.

In one embodiment, there is provided a process of any previous embodiment, wherein the diene comprises 1,5-cyclooctadiene; 1,5-dimethyl-1,5-cyclooctadiene; 1,6-dimethyl-1,5-cyclooctadiene, or a combination of two or more thereof.

In one embodiment, there is provided a process of any previous embodiment, wherein the ratio of total moles of cyclodiene additive to moles of platinum is less than 2:1.

In one embodiment, there is provided a process of any previous embodiment, wherein the ratio of total moles of cyclodiene additive to moles of platinum is from about 0.1:1 to about 2:1.

In one embodiment, there is provided a process of any previous embodiment, wherein the platinum compound is a Pt(0) compound, and the ratio of total moles of cyclodiene additive to moles of platinum is from about 0.1:1 to about 100:1.

In one embodiment, there is provided a process of any previous embodiment, wherein the platinum compound is chosen from Karstedt's catalyst, Ashby's catalyst, or a combination thereof.

In one embodiment, there is provided a process of any previous embodiment, wherein the silylhydride is chosen from a compound of the formula R$^9{}_m$SiH$_p$X$_{4-(m+p)}$ and/or M$_a$M$^H{}_b$D$_c$D$^H{}_d$T$_e$T$^H{}_f$Q$_g$, where each R$^9$ is independently a substituted or unsubstituted aliphatic or aromatic hydrocarbyl group, X is alkoxy, acyloxy, halogen, or silazane, m is 1-3, p is 1-3 the subscripts a, b, c, d, e, f, and g are such that the molar mass of the silylhydride is between 100 and 100,000 Dalton; M represents a monofunctional group of formula R$^{10}{}_3$SiO$_{1/2}$, a D represents a difunctional group of formula R$^{11}{}_2$SiO$_{2/2}$, a T represents a trifunctional group of formula R$^{12}$SiO$_{3/2}$, Q represents a tetrafunctional group of formula SiO$_{4/2}$, M$^H$ represents HR$^{13}{}_2$SiO$_{1/2}$, T$^H$ represents HSiO$_{3/2}$, and D$^H$ represents R$^{14}$HSiO$_{2/2}$; each occurrence of R$^{10-14}$ is independently C1-C18 alkyl, C1-C18 substituted alkyl, C6-C14 aryl or substituted aryl, wherein R10-14 optionally contains at least one heteroatom.

In one embodiment, there is provided a process of any previous embodiment, wherein the alkenyl silicone comprises at least two unsaturated groups and has a viscosity of at least 50 cps at 25° C.

In one embodiment, there is provided a process of any previous embodiment, wherein the alkenyl silicone is of the formula:

$$M^{vi}{}_a T_b D_c M_d Q_e$$

wherein M$^{vi}{}_a$=R$^{31}{}_2$R$^{32}$SiO$_{1/2}$; T$_b$=R$^{33}$SiO$_{3/2}$ where R$^{33}$ is chosen from R$^{31}$ or R$^{32}$; D$_c$=R$^{31}$R$^{33}$SiO$_{2/2}$ where R$^{33}$ is chosen from R$^{31}$ or R$^{32}$; M$_d$=R$^{31}{}_3$SiO$_{1/2}$; and Q$_e$=SiO$_{4/2}$; R$^{31}$ is independently selected from a monovalent hydrocarbon radical having one to forty carbon, optionally containing at least one heteroatom; and R$^{32}$ is selected from a terminal olefinic monovalent hydrocarbon radical having two to forty carbon atoms, optionally containing at least one heteroatom, and the alkenyl silicone is such as to provide at least two unsaturated groups reactive to hydrosilylation per chain; a≥0, b≥0, d≥0, e≥0; and the sum a+b+c+d+e is in the range 50-20,000.

In one embodiment, there is provided a process of any previous embodiment, wherein the inhibitor (e) is chosen from ethylenically unsaturated amides, aromatically unsaturated amides, acetylenic compounds, ethylenically unsaturated isocyanates, olefinic siloxanes, unsaturated hydrocarbon diesters, unsaturated hydrocarbon mono-esters of unsaturated acids, conjugated ene-ynes, hydroperoxides, ketones, sulfoxides, amine, phosphines, phosphites, nitrites, diaziridines, or a combination of two or more thereof.

In one embodiment, there is provided a process of any previous embodiment, wherein the concentration of platinum is from about 100 parts per billion (ppb) to about 100 ppm.

In one embodiment, there is provided a process of any previous embodiment, wherein component (e) is present in an amount of from about 0 to about 10 weight percent.

In one embodiment, there is provided a process of any previous embodiment, wherein components (a)-(e) are provided in a single composition.

In one embodiment, there is provided a process of any previous embodiment, wherein the reaction is completed in about 10 seconds or less.

In one embodiment, there is provided a process of any previous embodiment, wherein the process is conducted by heating at a temperature above room temperature.

In one embodiment, there is provided a process of any previous embodiment, wherein a composition of components (a)-(e) has a working life of at least 2 hours when the concentration of inhibitor (c) is about 0.25 weight percent or less.

In another aspect, the present invention provides a composition comprising (a) a silyl hydride, (b) an alkenyl silicone compound, (c) a platinum compound, (d) a cyclodiene, and (e) optionally an inhibitor, where the cyclodiene (d) is a compound of the formula:

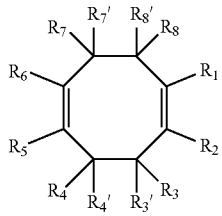

wherein $R^1$-$R^8$, $R^{3'}$, $R^{4'}$, $R^{7'}$, and $R^{8'}$ are independently hydrogen; an substituted or unsubstituted alkyl or aryl group optionally containing at least one heteroatom; an alkoxy; and a halogen radical; optionally $R^1$-$R^2$ and/or $R^5$-$R^6$ taken together may form a saturated or unsaturated ring structure.

In one embodiment, there is provided a composition of any previous embodiment, wherein the diene comprises 1,5-cyclooctadiene; 1,5-dimethyl-1,5-cyclooctadiene; 1,6-dimethyl-1,5-cyclooctadiene, or a combination of two or more thereof.

In one embodiment, there is provided a composition of any previous embodiment, wherein the ratio of total moles of cyclodiene additive to moles of platinum is less than 2:1.

In one embodiment, there is provided a composition of any previous embodiment, wherein the ratio of total moles of cyclodiene additive to moles of platinum is from about 0.1:1 to about 2:1.

In one embodiment, there is provided a composition of any previous embodiment, wherein the platinum compound is a Pt(0) compound, and the ratio of total moles of cyclodiene additive to moles of platinum is from about 0.1:1 to about 100:1.

In one embodiment, there is provided a composition of any previous embodiment, wherein the platinum compound is chosen from Karstedt's catalyst, Ashby's catalyst, or a combination thereof.

In one embodiment, there is provided a composition of any previous embodiment, wherein the silylhydride is chosen from a compound of the formula $R^9_m SiH_p X_{4-(m+p)}$ and/or $M_a M^H_b D_c D^H_d T_e T^H_f Q_g$, where each $R^9$ is independently a substituted or unsubstituted aliphatic or aromatic hydrocarbyl group, X is alkoxy, acyloxy, halogen, or silazane, m is 1-3, p is 1-3 the subscripts a, b, c, d, e, f, and g are such that the molar mass of the silylhydride is between 100 and 100,000 Dalton; M represents a monofunctional group of formula $R^{10}_3 SiO_{1/2}$, a D represents a difunctional group of formula $R^{11}_2 SiO_{2/2}$, a T represents a trifunctional group of formula $R^{12} SiO_{3/2}$, Q represents a tetrafunctional group of formula $SiO_{4/2}$, $M^H$ represents $HR^{13}_2 SiO_{1/2}$ $T^H$ represents $HSiO_{3/2}$, and $D^H$ represents $R^{14} HSi)_{2/2}$; each occurrence of $R^{10-14}$ is independently C1-C18 alkyl, C1-C18 substituted alkyl, C6-C14 aryl or substituted aryl, wherein R10-14 optionally contains at least one heteroatom.

In one embodiment, there is provided a composition of any previous embodiment, wherein the alkenyl silicone comprises at least two unsaturated groups and has a viscosity of at least 50 cps at 25° C.

In one embodiment, there is provided a composition of any previous embodiment, wherein the alkenyl silicone is chosen from an compound of the formula:

wherein $M^{vi}_a = R^{31}_2 R^{32} SiO_{1/2}$; $T_b = R^{33} SiO_{3/2}$ where $R^{33}$ is chosen from $R^{31}$ or $R^{32}$; $D_c = R^{31} R^{33} SiO_{2/2}$ where $R^{33}$ is chosen from $R^{31}$ or $R^{32}$; $M_d = R^{31}_3 SiO_{1/2}$; and $Q_e = SiO_{4/2}$; $R^{31}$ is independently selected from a monovalent hydrocarbon radical having one to forty carbon, optionally containing at least one heteroatom; and $R^{32}$ is selected from a terminal olefinic monovalent hydrocarbon radical having two to forty carbon atoms, optionally containing at least one heteroatom. The composition of the alkenyl silicone is such as to provide at least two unsaturated groups reactive to hydrosilylation per chain; a≥0, b≥0; d≥0, e≥0; values for c in particular are determined by the desired properties and attributes of the cross-linked material so that the sum a+b+c+d+e is in the range 50-20,000.

In one embodiment, there is provided a composition of any previous embodiment comprising a cure inhibitor (e) chosen from an ethylenically unsaturated amide, an aromatically unsaturated amide, an acetylenic compound, an ethylenically unsaturated isocyanate, an olefinic siloxane, an unsaturated hydrocarbon diester, an unsaturated hydrocarbon mono-ester of an unsaturated acid, an unsaturated anhydride, a conjugated ene-yne, a hydroperoxide, a ketone, a sulfoxide, an amine, a phosphine, a phosphite, a nitrite, a diaziridine, or a combination of two or more thereof.

In one embodiment, there is provided a composition of any previous embodiment, wherein the concentration of platinum is from about 100 parts per billion (ppb) to about 100 ppm.

In one embodiment, there is provided a composition of any previous embodiment, wherein component (e) is present in an amount of from about 0 to about 10 weight percent.

In one embodiment, there is provided a composition of any previous embodiment, wherein components (a)-(e) are provided in a single composition.

In still another aspect, the present invention provides a cured material prepared from a composition according any previous embodiment.

In one embodiment, the cured material comprises the cyclodiene component (d).

In yet another aspect, the present invention provides a coating formed from the composition of any previous embodiment.

In another aspect, the present invention provides a substrate having a surface thereof at least partially coated with a coating formed from the composition of any previous embodiment. In one embodiment, the coating is anchored to the surface of the substrate.

With respect to cure processes and compositions, it has been found that when the platinum compound is a Pt(0) compound, the ratio of total moles of cyclodiene additive to moles of platinum can be varied. In on embodiment, when the platinum compound is a Pt(0) compound, the ratio of total moles of cyclodiene additive to moles of platinum is from about 0.1:1 to about 100:1; even from about 1:1 to about 5:1.

DETAILED DESCRIPTION

Figure 1:
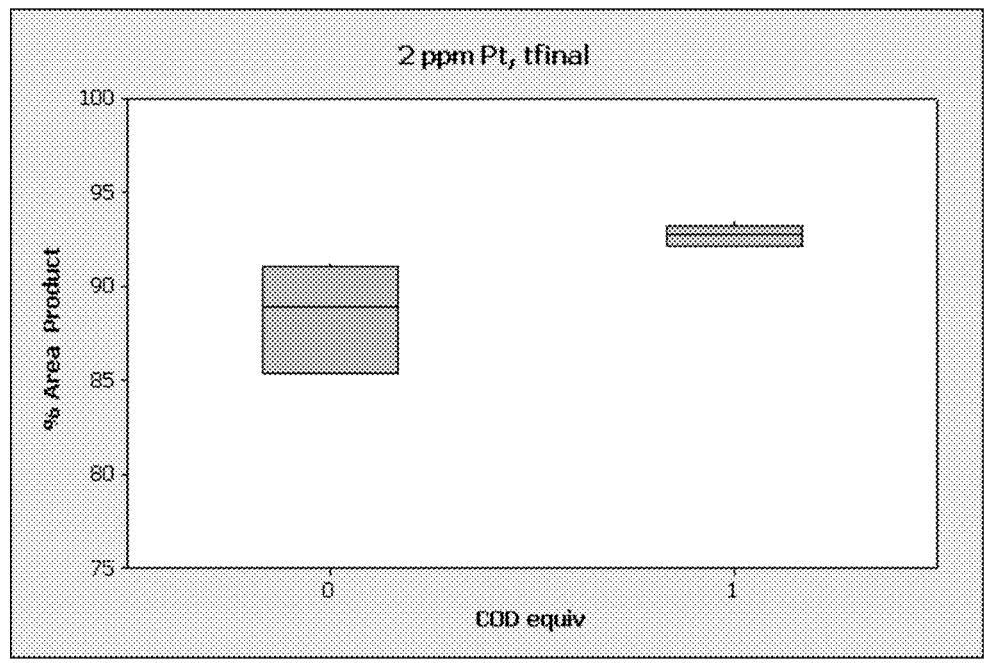
FIG. 1 is a graph showing the product yield for reactions of allyl methacrylate and SiMeCl$_2$H as determined by GC analysis for reactions runs with and without COD additives.

The present invention provides a process and compositions for the hydrosilylation of a composition containing a silylhydride and a compound containing at least one unsaturated group in the presence of a platinum catalyst and cyclodiene compound.

The cyclodiene of this invention is represented by Formula I:

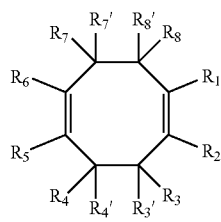

Formula I wherein $R^1$-$R^8$, $R^{3'}$, $R^{4'}$, $R^{7'}$, and $R^{8'}$ are independently a H or substituted or unsubstituted alkyl or aryl group optionally containing at least one heteroatom. $R^1$-$R^8$ also independently represent a halide or alkoxy group. Furthermore, $R^1$-$R^2$ and $R^5$-$R^6$ taken together, or independently, may form a ring. Examples of suitable compounds of Formula I, include but are not limited to, 1,5-cyclooctadiene, 1,5-dimethyl-1,5-cyclooctadiene, 1,6-dimethyl-1,5-cyclooctadiene, and mixtures of two or more thereof.

The cyclodiene additive is provided such that the molar equivalent ratio of cyclodiene additive to platinum is less than 3:1 for Pt(II) or Pt(IV) compounds and precatalysts. In one embodiment, the ratio is 2:1, 1.5:1 1:1; 0.5:1; even 0.1:1.

In one embodiment, the cyclodiene to platinum ratio is from about 0.1:1 to about 2:1; from about 0.25:1 to about 1.5:1; even from about 0.5:1 to about 1:1. It will be appreciated that the ratio of cyclodiene to platinum includes all fractional ratios within the particular ranges. The total moles of cyclodiene provided to the process include the cyclodiene-platinum complex plus any additional non-complexed cyclodiene present in the process. Thus, where the process employs a cyclodiene-platinum complex as the catalyst, the additional non-complexed cyclodiene may be added to the process separate from the cyclodiene-platinum complex or may be provided to the process as a mixture with the cyclodiene-platinum complex. When the catalyst is a cyclodiene-platinum complex, it is desirable that the non-complexed cyclodiene be the same as that already complexed with the platinum although this is not a strict requirement. For Pt(0) compounds and precatalysts, the cyclodiene additive is provided such that the molar equivalent ratio of cyclodiene additive to Pt is 0.1:1 to about 100:1. In one embodiment, the molar equivalent ratio of cyclodiene additive to Pt(0) is from about 1:1 to about 75:1; from about 2:1 to about 50:1; from about 3:1 to about 25:1; even from about 5:1 to about 15:1. In still other embodiments, the molar equivalent ratio of cyclodiene additive to Pt(0) is from about 1:1 to about 10:1; from about 2:1 to about 7.5:1; even from about 3:1 to about 5:1. The practical, usable ratio for a particular Pt(0) system and application is determined by signs of detrimental effects such as undesirably slow reaction speed, odor and other negative effects.

The silyl hydride and/or hydrosiloxane employed in the reactions is not particularly limited. It can be, for example, any compound chosen from hydrosilanes or hydrosiloxanes including those compounds of the formulas $R^9{}_mSiH_pX_{4-(m+p)}$ or $M_aM^H{}_bD_cD^H{}_dT_eT^H{}_fQ_g$, where each $R^9$ is independently a substituted or unsubstituted aliphatic or aromatic hydrocarbyl group, X is halide, alkoxy, acyloxy, or silazane, m is 1-3, p is 1-3, and M, D, T, and Q have their usual meaning in siloxane nomenclature, with the proviso that when X is halide, the unsaturated substrate is not an alkyne. The subscripts a, b, c, d, e, f, and g are such that the molar mass of the siloxane-type reactant is between 100 and 100,000 Dalton. In one embodiment, an "M" group represents a monofunctional group of formula $R^{10}{}_3SiO_{1/2}$, a "D" group represents a difunctional group of formula $R^{11}{}_2SiO_{2/2}$, a "T" group represents a trifunctional group of formula $R^{12}SiO_{3/2}$, and a "Q" group represents a tetrafunctional group of formula $SiO_{4/2}$, an "$M^H$" group represents $HR^{13}{}_2SiO_{1/2}$, a "$T^H$" represents $HSiO_{3/2}$, and a "$D^H$" group represents $R^{14}HSiO_{2/2}$. Each occurrence of $R^{10\text{-}14}$ is independently C1-C18 alkyl, C1-C18 substituted alkyl, C6-C14 aryl or substituted aryl, wherein $R^{10\text{-}14}$ optionally contains at least one heteroatom.

The present invention also provides hydrosilylation with hydridosiloxanes comprising carbosiloxane linkages (for example, Si—CH$_2$—Si—O—SiH, Si—CH$_2$—CH$_2$—Si—O—SiH or Si-arylene-Si—O—SiH). Carbosiloxanes contain both the —Si-(hydrocarbylene)-Si— and —Si—O—Si— functionalities, where hydrocarbylene represents a substituted or unsubstituted, divalent alkylene, cycloalkylene or arylene group. The synthesis of carbosiloxanes is disclosed in U.S. Pat. Nos. 7,259,220; 7,326,761 and 7,507,775 all of which are incorporated herein in their entirety by reference. An exemplary formula for hydridosiloxanes with carbosiloxane linkages is $R^{15}R^{16}R^{17}Si(CH_2R^{18})_xSiOSiR^{19}R^{20}(OSiR^{21}R^{22})_yOSiR^{23}R^{24}H$, wherein $R^{15}R^{24}$ is independently a monovalent alkyl, cycloalkyl or aryl group such as methyl, ethyl, cyclohexyl or phenyl.

Additionally, $R^{15-24}$ independently may also be H. The subscript x has a value of 1-8, y has a value from zero to 10 and is preferably zero to 4. A specific example of a hydridocarbosiloxane is $(CH_3)_3SiCH_2CH_2Si(CH_3)_2OSi(CH_3)_2H$.

As used herein, "unsaturated" refers to a compound comprising one or more double or triple bonds. In one embodiment, unsaturated refers to a compound comprising carbon-carbon double or triple bonds. The unsaturated compound containing at least one unsaturated functional group employed in the hydrosilylation reaction is generally not limited and can be chosen from an unsaturated compound as desired for a particular purpose or intended application. The unsaturated compound can be a mono-unsaturated compound or it can comprise two or more unsaturated functional groups. In one embodiment, the unsaturated group can be an aliphatically unsaturated functional group. Examples of suitable compounds containing an unsaturated group include, but are not limited to, unsaturated polyethers such as alkyl-capped allyl polyethers, vinyl functionalized alkyl capped allyl or methylallyl polyethers; terminally unsaturated amines; alkynes (except with hydrochlorosilanes); C2-C45 linear or branched olefins, in one embodiment alpha olefins; terminally unsaturated dienes; unsaturated epoxides such as allyl glycidyl ether and vinyl cyclohexene-oxide; terminally unsaturated acrylates or methacrylates; unsaturated aryl ethers; aliphatically unsaturated aromatic hydrocarbons; unsaturated cycloalkanes such as trivinyl cyclohexane; vinyl-functionalized polymer or oligomer; vinyl-functionalized and/or terminally unsaturated allyl-functionalized silane and/or vinyl-functionalized silicones; unsaturated fatty acids; unsaturated fatty esters; or combinations of two or more thereof. Illustrative examples of such unsaturated substrates include, but are not limited to, ethylene, propylene, isobutylene, 1-hexene, 1-octene, 1-octadecene, styrene, alpha-methylstyrene, cyclopentene, norbornene, 1,5-hexadiene, norbornadiene, vinylcyclohexene, allyl alcohol, allyl-terminated polyethyleneglycol, allylacrylate, allyl methacrylate, allyl glycidyl ether, allyl-terminated isocyanate- or acrylate prepolymers, polybutadiene, allylamine, methallyl amine, methyl undecenoate, acetylene, phenylacetylene, vinyl-pendent or vinyl-terminal polysiloxanes, vinylcyclosiloxanes, vinylsiloxane resins, other terminally-unsaturated alkenyl silanes or siloxanes, vinyl-functional synthetic or natural minerals, etc.

Unsaturated polyethers suitable for the hydrosilylation reaction include polyoxyalkylenes having the general formula:

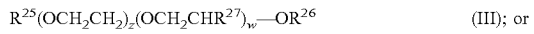  (III); or

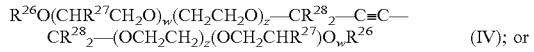  (IV); or

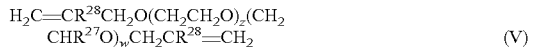  (V)

wherein $R^{25}$ denotes an unsaturated organic group containing from 2 to 10 carbon atoms such as vinyl, allyl, methallyl, propargyl or 3-pentynyl. When the unsaturation is olefinic, it is desirably terminal to facilitate smooth hydrosilylation. However, when the unsaturation is a triple bond, it may be internal. $R^{26}$ is independently hydrogen, an alkyl group, e.g., from 1 to 8 carbon atoms such as the alkyl groups $CH_3$, n-$C_4H_9$, t-$C_4H_9$ or i-$C_8H_{17}$, and an acyl group, e.g., $CH_3COO$, t-$C_4H_9COO$, the beta-ketoester group such as $CH_3C(O)CH_2C(O)O$, or a trialkylsilyl group. $R^{27}$ and $R^{28}$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl groups, for example, benzyl, phenylethyl and nonylphenyl, or the cycloalkyl groups, for example, cyclohexyl and cyclooctyl. $R^{28}$ may also be hydrogen. Methyl is the most preferred $R^{27}$ and $R^{28}$ groups. Each occurrence of z is 0 to 100 inclusive and each occurrence of w is 0 to 100 inclusive. Preferred values of z and w are 1 to 50 inclusive.

In one embodiment, the unsaturated compound is chosen from an alkenyl silicone. The alkenyl silicone may be an alkenyl functional silane or siloxane that is reactive to hydrosilylation. The alkenyl silicone may be cyclic, aromatic, or a terminally-unsaturated alkenyl silane or siloxane. The alkenyl silicone may be chosen as desired for a particular purpose or intended application. In one embodiment the alkenyl silicone comprises at least two unsaturated groups and has a viscosity of at least about 50 cps at 25° C. In one embodiment the alkenyl silicone has a viscosity of at least about 75 cps at 25° C.; at least about 100 cps at 25° C.; at least 200 cps at 25 25° C.; even at least about 500 cps at 25° C. Here as elsewhere in the specification and claims, numerical values may be combined to form new and non-disclosed ranges.

In one embodiment, the alkenyl silicone is a compound of the formula:

the alkenyl silicone is of the formula:

wherein $M^{vi}_a = R^{31}_2R^{32}SiO_{1/2}$; $T_b = R^{33}SiO_{3/2}$ where $R^{33}$ is chosen from $R^{31}$ or $R^{32}$; $D_c = R^{31}R^{33}SiO_{2/2}$ where $R^{33}$ is chosen from $R^{31}$ or $R^{32}$; $M_d = R^{31}_3SiO_{1/2}$; and $Q_e = SiO_{4/2}$; $R^{31}$ is independently selected from a monovalent hydrocarbon radical having one to forty carbon, optionally containing at least one heteroatom; and $R^{32}$ is selected from a terminal olefinic monovalent hydrocarbon radical having two to forty carbon atoms, optionally containing at least one heteroatom. The composition of the alkenyl silicone is such as to provide at least two unsaturated groups reactive to hydrosilylation per chain; a≥0, b≥0, d≥0, e≥0; values for c in particular are determined by the desired properties and attributes of the cross-linked material so that the sum a+b+c+d+e is in the range 50-20,000. Particular alkenyl silicones and cross-linkers chosen to generate desired mechanical, thermal and other properties of the product can be determined by those skilled in the art. Terminally-unsaturated alkenyl silicone materials are particularly suitable for forming cured or crosslinked products such as coatings and elastomers. It is also understood that two or more of these alkenyl silicones, independently selected, may be used in admixture in a cure formulation to provide desired properties.

In accordance with aspects of the present technology, when the unsaturated compound is a terminal alkyne, the silylhydride is a silylhydride other than a halosilane.

The present process can also be used, for example, for preparing a silylated polyurethane. This may include the step of contacting a terminally-unsaturated polyurethane with a silylhydride in the present of a platinum catalyst and the cyclodiene additive.

The hydrosilylation process is conducted in the presence of a platinum catalyst. The platinum catalyst employed in the process is not particularly limited and can be chosen from a variety of platinum compounds including, but not limited to, platinum halides, platinum siloxane complexes such as Ashby's or Karstedt's catalyst, cycloalkadiene-platinum complexes, or various other common platinum compounds or complexes known in the art.

In one embodiment, the platinum catalyst comprises a platinum halide, a reaction product of a platinum halide and organosilicon compound having terminal aliphatic unsaturation, or combinations of two or more thereof. Suitable platinum halides include, but are not limited to, platinum dichloride, platinum dibromide, platinum tetrachloride, chloroplatinic acid (i.e. $H_2PtCl_6 \cdot 6H_2O$), dipotassium tetrachloroplatinate (i.e. $K_2PtCl_4$), etc. A particularly suitable platinum halide is chloroplatinic acid. Platinum catalysts useful in the present invention also include the reaction product of a platinum halide with an organosilicon compound having terminal aliphatic unsaturation. Such catalysts are described, for example, in Willing, U.S. Pat. No. 3,419,593, which is incorporated by reference for its teaching of platinum catalysts useful in the present process. The platinum catalyst can be, for example, the reaction product of a solution of chloroplatinic acid in ethanol or 2-propanol optionally in combination with an ethereal solvent at various ratios, or the reaction products of platinum dichloride or chloroplatinic acid with 1,3-divinyl-1,1,3,3-tetramethyldisiloxane.

In one embodiment, the platinum catalyst comprises a cycloalkadiene-platinum complex described by formula or $Pt(R^{30})X_2$, where $R^{30}$ is a cycloalkadiene comprising about six to 20 carbon atoms and each X can be an independently selected halogen atom. In one embodiment, the cycloalkadiene comprises about 6 to 10 carbon atoms. Suitable cycloalkadienes for the cycloalkadiene-platinum complexes include, but are not limited to, cyclohexadiene, cycloheptadiene, cyclooctadiene, cyclodecadiene, dicyclopentadiene and norbornadiene. 1,5-cyclooctadiene is a particularly suitable cycloalkadiene for the cycloalkadiene-platinum complexes. In one embodiment, the platinum catalyst is described by formula $Pt(R^{30})Cl_2$, where $R^{30}$ is 1,5-cyclooctadiene.

The concentration of platinum catalyst used in the present process can be varied. In one embodiment, the concentration of platinum is from about 100 parts per billion (ppb) to about 100 ppm; from about 500 ppb to about 70 ppm; from about 1 ppm to about 50 ppm; even from about 10 ppm to about 30 ppm. Here as elsewhere in the specification and claims, numerical values can be combined to form new and alternative ranges.

The platinum catalyst may be dissolved in solvent to improve ease of handling. The solvent is not limited and can be either polar or non-polar. Any solvent can be used in the method of the invention, as long as it facilitates the dissolution of the platinum catalyst, without deleterious effects.

The temperature range for the process of the hydrosilylation is from −50° C. to 250° C., preferably from 0° C. to 150° C. A variety of reactors can be used in the process of this invention. The process can be run as a batch reaction or a continuous reaction at ambient, sub-ambient, or supra-ambient pressures. In one embodiment, the reaction is carried out under an inert atmosphere. Selection is determined by factors such as the volatility of the reagents and products. Continuously stirred batch reactors are conveniently used when the reagents are liquid at ambient and reaction temperature. These reactors can also be operated with a continuous input of reagents and continuous withdrawal of dehydrogenatively silylated or hydrosilylated reaction product. With gaseous or volatile olefins and silanes, fluidized-bed reactors, fixed-bed reactors and autoclave reactors can be more appropriate.

Compositions and processes for forming cured or cross-linked products may include a cure inhibitor (e) Examples of suitable inhibitors include, but are not limited to, ethylenically unsaturated amides, aromatically unsaturated amides, acetylenic compounds, ethylenically unsaturated isocyanates, olefinic siloxanes, unsaturated hydrocarbon diesters, unsaturated hydrocarbon mono-esters of unsaturated acids, unsaturated anhydrides, conjugated ene-ynes, hydroperoxides, ketones, sulfoxides, amine, phosphines, phosphites, nitrites, diaziridines, etc. Particularly suitable inhibitors for the compositions are alkynyl alcohols and maleates.

The amount of inhibitor to be used in the compositions is not critical and can be any amount that will retard the above described platinum catalyzed hydrosilylation reaction at room temperature while not preventing said reaction at moderately elevated temperature, i.e. a temperature that is 25 to 125° C. above room temperature. No specific amount of inhibitor can be suggested to obtain a specified bath life at room temperature since the desired amount of any particular inhibitor to be used will depend upon the concentration and type of the platinum metal containing catalyst, the nature and amounts of components a and b. The range of component (e) can be 0 to about 10% weight, about 0.001 wt to 2% by weight, even about 0.12 to about 1 by weight. Here as elsewhere in the specification and claims, numerical values can be combined to form new and alternative ranges. In one embodiment, the compositions can be free of any inhibitor component (e).

The composition may optionally further comprise one or more additional ingredients, such as filler, filler treating agent, plasticizer, spacer, extender, biocide, stabilizer, flame retardant, surface modifier, pigment, anti-aging additive, rheological additive, corrosion inhibitor, surfactant or combination thereof.

Accordingly, in some embodiments, the present invention is also directed to the compositions produced from the above described methods. These compositions contain the hydrosilylated products of the silylhydride and the compound having at least one unsaturated group. The hydrosilylated products that are produced by the process of the present invention have uses in the synthesis of silicone materials such as organosilanes for coupling agents, adhesives, products for agricultural and personal care applications, and silicone surfactant for stabilizing polyurethane foams as well as use as silicone materials such as elastomers, coatings, e.g., release liner coatings, for molding etc. When provided as a coating, the composition is coated onto at least a portion of a surface of a substrate. The amount of the surface coated with the coating composition can be selected as desired for a particular purpose or intended application. Release coatings are part of a laminate wherein a release coating is coated upon a substrate. Generally substrates suitable for release coatings include, but are not limited to, paper, polymeric films such as those consisting of polyethylene, polypropylene, polyester, etc. The use of the present catalysts in coating compositions has been found to provide particularly good curing in a short period of time including in about 10 seconds or less; about 7 seconds or less, even about 5 seconds or less. In one embodiment, curing can be effected in about 1 to about 10 seconds, 1 to about 5 seconds, even about 1-2 seconds. Further, the cured compositions exhibit good binding and can be anchored to substrates including, for example, to paper.

The following examples are intended to illustrate, but in no way limit the scope of the present invention. All parts and percentages are by weight and all temperatures are in Celsius unless explicitly stated otherwise. All patents, other publications, and U.S. patent applications referred to in the instant application are incorporated herein by reference in their entireties.

EXAMPLES

Reactions and manipulations were performed under nitrogen, using standard Schlenk-line techniques. The chloroplatinic acid was employed as an alcoholic solution of hexachloroplatinic acid. COD was used either directly or as an alcoholic solution. The 3,5-dimethylhex-1-yn-3-ol (S61), 1-ethynyl-1-cyclohexanol (ECH), allylpolyether, MD$^H$M, SilForce® SL6020 and SL6900 were obtained for Momentive Performance Materials. All other starting materials were purchased from a commercial source and used as received without further purification.

Example 1: Hydrosilylation of Allyl Methacrylate (AMA) with SiMeCl$_2$H Using Diene Additives A 4-neck round bottomed flask was fitted with an addition funnel, a syringe port, an alcohol thermometer, a magnetic stir bar, and a straight water-condenser fitted on top with a dry ice condenser. The addition funnel was equipped with a N$_2$ inlet and the N$_2$ line was split with a t-piece attached to a bubbler before the reaction. The system was flushed with N$_2$ and was charged with the appropriate inhibitors. The SiMeCl$_2$H (16.5 g, 0.140 mol) was charged to the addition funnel. The round bottomed flask was charged with allyl methacrylate (19.7 g, 0.16 mol), chloroplatinic acid (2 ppm Pt), and cyclooctadiene (COD) solution in ethanol (0.39 μmol, equimolar to Pt), where COD was used as an additive. The reaction mixture was heated to 80° C. Approximately 1 mL of the chlorosilane was added and the reaction was monitored for an exotherm. Once an exothermic reaction was detected, the chlorosilane was slowly added as to maintain a reaction temperature between 80° C. and 90° C. After chlorosilane addition was complete, the reaction was heated to 80° C. for 90 min. After 90 min the heat was removed and the product at ambient temperature was decanted into a brown bottle and stored under a N$_2$ blanket. The material was analyzed by GC and NMR spectroscopy.

Figure 2:
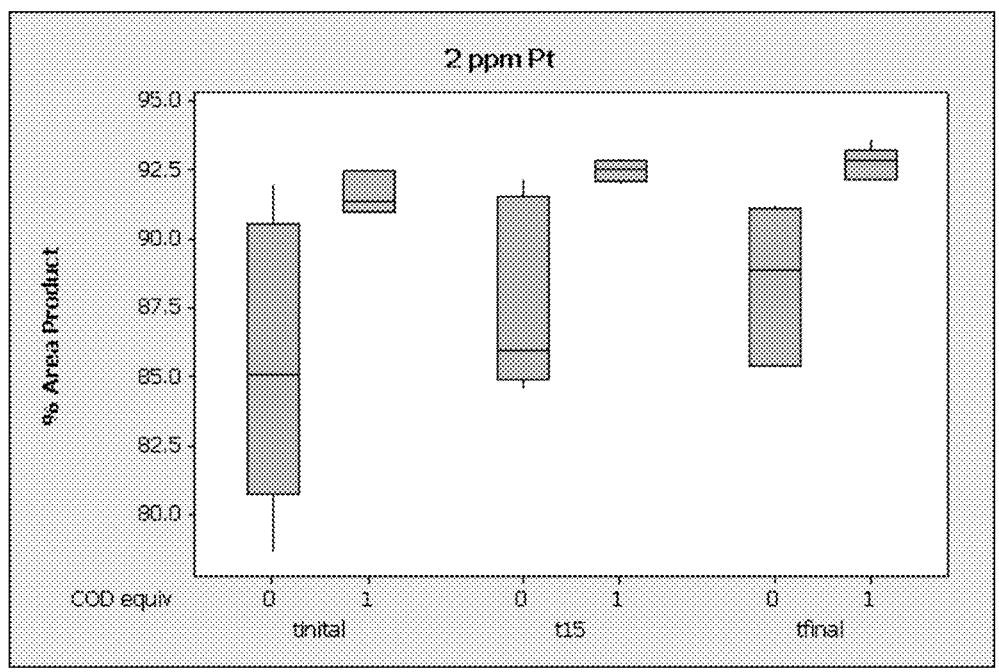
FIG. 2 is a graph showing the product yield for reactions of allyl methacrylate and SiMeCl$_2$H over time for reactions run with and without COD additives.

Comparative Example 1: Hydrosilylation of Allyl Methacrylate with SiMeCl$_2$H without the Use of Diene Additives A reaction was run similarly to Example 1 except that COD solution was not added to the reaction. FIG. 1 shows the product yield evaluated by GC analysis for reactions run with and without COD additives at 2 ppm of platinum. FIG. 2 shows the product the product yield over time with and without COD additives. Aliquots were taken and analyzed by GC immediately after chlorosilane addition was complete (t initial), 15 minutes after chlorosilane addition was complete (t 15), and 90 minutes after chlorosilane addition was complete (t final).

Example 2: Hydrosilylation of Allyl Methacrylate with SiMeCl$_2$H Using Diene Additives Run to Evaluate the Color of the Reaction Product The reactions were run at a 5 ppm Pt loading similar to those discussed above, except the inhibitors which impart color were not added to the reaction. The color of the product was evaluated for reactions of allyl methacrylate and SiMeCl$_2$H run with various amount of COD equivalents.

TABLE 1

| COD equiv | Color (Pt/Co) |
|---|---|
| 0 | 331 |
| 0 | 193 |

TABLE 1-continued

| COD equiv | Color (Pt/Co) |
|---|---|
| 0.5 | 150 |
| 1 | 46 |

Example 3: Hydrosilylation of Allyl Methacrylate with Si(OEt)$_3$H Using Diene Additives A 4-neck round bottomed flask equipped with a magnetic stir bar, straight condenser, topped with a dry-ice condenser, syringe port, a liquid addition funnel, and a thermometer and placed under N$_2$. The reaction vessel was charged with inhibitors and allyl methacrylate (15 mL, 0.11 mol), the chloroplatinic acid solution (2 ppm Pt) COD solution (equimolar to Pt). The addition funnel was charged with the triethoxysilane (19 mL, 0.1 mol). The reaction was heated to 90° C. and then an aliquot of the triethoxysilane (3-5% by volume) was added and the reaction was monitored for exotherm. After exotherm is confirmed the remainder of the triethoxysilane was added via addition funnel at a rate to keep the reaction between 85° C. and 95° C. After final addition of the triethoxysilane, the reaction was heated for 90 minutes at 90° C. The resulting product was analyzed by GC and $^1$H NMR. The average Hazen value of the product for 4 separate runs was 111 Pt/Co.

Figure 3:
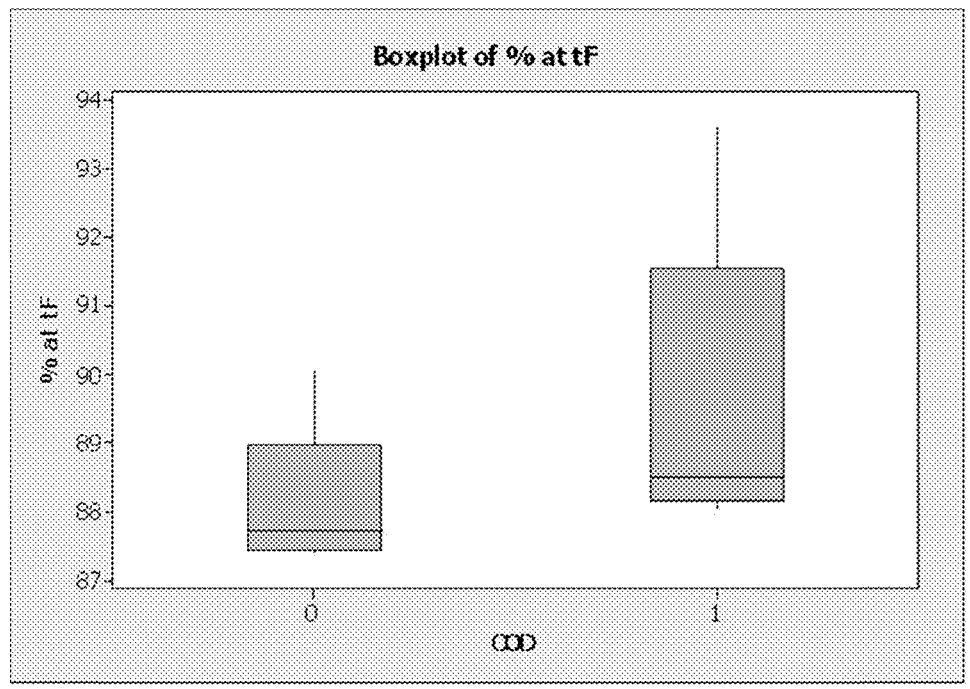
FIG. 3 is a graph showing the product yield for reactions of allyl methacrylate and Si(OEt)$_3$H as determined by GC analysis for reactions runs with and without COD additives.

Comparative Example 2: Hydrosilylation of Allyl Methacrylate with Si(OEt)$_3$H without the Use of Diene Additives A reaction was run similarly as in Example 3 except that COD solution was not added to the reaction. The average Hazen value of the product for 4 separate runs was 171 Pt/Co. FIG. 3 compares the product yield as determined by GC analysis for Example 3 and Comparative Example 2 at 2 ppm of platinum.

Example 4: Hydrosilylation of Allylpolyether with MD$^H$M Using Diene Additives A 4-neck round bottomed flask was equipped with a magnetic stir bar, an addition funnel, a syringe port, an alcohol thermometer, and a straight water-condenser fitted with a t-piece to accommodate N$_2$ flow. The system was flushed with N$_2$ and was charged with the MD$^H$M (5 mL, 0.02 mol) and methoxypolyethyleneglycolallylether (39.4 g, 0.1 mol). The remaining MD$^H$M (15 mL, 0.06 mol) was charged to the addition funnel. The round bottomed flask was charged with the COD solution (1.76 μmol, equimolar to Pt). The reaction mixture was heated to 80° C. The chloroplatinic acid solution (6 ppm Pt) was added to the mixture. The MD$^H$M was slowly added as to maintain a reaction temperature below 120° C. After addition of the MD$^H$M was complete, the reaction was heated to 80° C. for 60 min. The material was analyzed by NMR spectroscopy. The average Hazen value of the product for 3 separate runs was 32 Pt/Co.

Comparative Example 3: Hydrosilylation of Allylpolyether with MD$^H$M without the Use of Diene Additives A reaction was run similarly to Example 4 except that COD solution was not added to the reaction. The average Hazen value of the product for 3 separate runs was 78 Pt/Co.

Example 5: Hydrosilylation of Allyl Glycidyl Ether (AGE) with Si(OEt)₃H Using Diene Additives A 4-neck round bottomed flask was equipped with a magnetic stir bar, a condenser, a septum, a liquid addition funnel, and a thermocouple and subsequently rendered inert with $N_2$. The reaction vessel was charged with AGE (44.6 g, 0.39 mol) and the liquid addition funnel was charged with triethoxysilane (53.4 g, 0.33 mol). Subsequently, 5% of the triethoxysilane volume was added to the reaction vessel and the mixture heated to 90° C. Glacial acetic acid (44 μL) and the appropriate amount of COD solution were injected via syringe, followed by the injection of the chloroplatinic acid catalyst solution (250 ppb Pt). After confirmation of a reaction exotherm, the remainder of the triethoxysilane was added via addition funnel at a rate aimed at keeping the reaction temperature between 85° C. and 95° C. After final addition of the triethoxysilane, the temperature was maintained at 90° C. for an additional 2 hours. The resulting product mixture was analyzed by GC for % product area.

Figure 4:
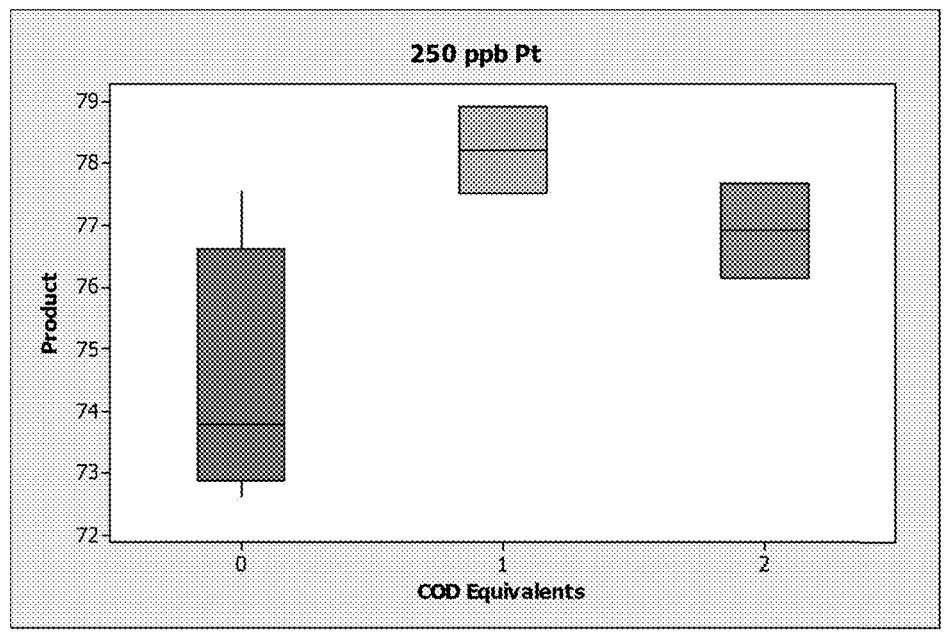
FIG. 4 is a graph showing the analyses of product mixtures for reactions of allyl glycidyl ether and Si(OEt)$_3$H run without COD and with 2 different ratios of COD to Pt.

Comparative Example 4: Hydrosilylation of Allyl Glycidyl Ether with Si(OEt)₃H without the Use of Diene Additives A reaction was run similarly as in Example 5 except that COD solution was not added to the reaction. FIG. 4 shows the product yield for Example 5 (at 1 and 2 equivalents of COD) and Comparative Example 4.

Example 6: Hydrosilylation of Allyl Methacrylate with SiCl₃H Using Diene Additives A 3-neck round bottomed flask was fitted with a syringe pump feeding across a septum, thermocouple connected to a temperature controller controlling a heating mantle, a magnetic stir bar, and a straight water-condenser fitted on top equipped with a $N_2$ inlet to a mineral oil bubbler. The system was flushed with $N_2$ and the round bottom flask was charged was charged with the allyl methacrylate (11.37 g, 0.09 mol) and appropriate inhibitors. The SiCl₃H was charged to the syringe pump. The syringe pump was set on a feed rate of 0.14 mL/min and total feed volume was set to 8.41 mL (11.27 g, 0.08 mol). The reaction mixture was heated to 80° C. At 80° C. the reaction mixture was charged with chloroplatinic acid solution (3.3 ppm Pt), and COD solution in ethanol (0.38 μmol, equimolar to Pt), where COD was used as an additive. The chlorosilane feed was started and added over 1 hour. The exotherm was seen and reached a maximum temperature of 94.7° C. after 7 minutes onto the addition. After chlorosilane addition was complete the reaction mixture was cooled to ambient temperature and analyzed by GC. The composition of the reaction mixture was 75.3% product.

Comparative Example 5: Hydrosilylation of Allyl Methacrylate with SiCl₃H without the Use of Diene Additives A 3-neck round bottomed flask was fitted with a syringe pump feeding across a septa, thermocouple connected to a temperature controller controlling a heating mantle, a magnetic stir bar, and a straight water-condenser fitted on top equipped with a $N_2$ inlet to a mineral oil bubbler. The system was flushed with $N_2$ and the round bottomed flask was charged was charged with the allyl methacrylate (11.37 g, 0.09 mol) and appropriate inhibitors. The SiCl₃H was charged to the syringe pump. The syringe pump was set on a feed rate of 0.14 mL/min and total feed volume was set to 8.41 mL (11.27 g, 0.08 mol). The reaction mixture was heated to 80° C. At 80° C. the reaction mixture was charged with chloroplatinic acid solution (6.5 ppm Pt). The chlorosilane feed was started and added over 1 hour. The exotherm was seen and reached a maximum temperature of 90.2° C. after 5 minutes onto the addition. After chlorosilane addition was complete the reaction mixture was cooled to ambient temperature and analyzed by GC. The composition of the reaction mixture was 73.2% product.

Examples 7-8: Hydrosilylation of an OH-Terminated Methallylpolyether with a Carbosiloxyhydride Examples 7 and 8 and Comparative Examples 6-7 illustrate the effective use of 1,5-cyclooctadiene (COD) in the platinum-catalyzed, solventless hydrosilylation of uncapped methallyl polyethers by the carbodisiloxane, $(CH_3)_3SiCH_2CH_2Si(CH_3)_2OSi(CH_3)_2H$. The reaction products are intermediates in the synthesis of materials useful for making contact lens (See U.S. Patent Publications 2012/0244088 and 2012/0245249)

The carbodisiloxane was synthesized as disclosed in U.S. Pat. No. 7,259,220. The polyethers were the four and ten ethoxylates of methallyl alcohol. The four ethoxylate has a molecular weight of 248.32. The ten ethoxylate has a molecular weight of 512.64. Each polyether was reacted with and without addition of COD. Karstedt's catalyst was the platinum source in each experiment.

TABLE 2

Quantities of Raw Materials Used in Examples 7 and 8 and Comparative Examples 6 and 7

|  | Comparative Example 6 | Example 7 | Comparative Example 7 | Example 8 |
| --- | --- | --- | --- | --- |
| Carbodisiloxane | 110.51 g<br>0.47 mole | 110.51 g<br>0.47 mole | 110.51 g<br>0.47 mole | 110.51 g<br>0.47 mole |
| Four ethoxylate of methallyl alcohol | 116.00 g<br>0.47 mole | 116.00 g<br>0.47 mole | | |
| Ten ethoxylate of methallyl alcohol | | | 240.00 g<br>0.47 mole | 240.00 g<br>0.47 mole |
| Karstedt's Catalyst | 25 ppm Pt | 25 ppm Pt | 25 ppm Pt | 25 ppm Pt |
| COD | None | 7 μL<br>(6.2 mg) | None | 7 μL<br>(6.2 mg) |
| SiH Test | Positive after 19 h reaction time | Negative after 19 h reaction time | Positive after 19 h reaction time | Negative after 19 h reaction time |

Each reaction was conducted in a 500 mL, 4-neck round bottomed flask fitted with a temperature-controlled heating mantle, mechanical stirrer, reflux condenser and Claisen connection. A serum cap was placed over the fourth neck. A thermocouple and nitrogen inlet line were affixed to the Claisen connection.

Equimolar quantities of carbodisiloxane and polyether were used because of the absence of isomerization with methallyl groups. In each experiment, the carbodisiloxane and polyether were added to the reaction flask and stirred vigorously while the environment in the flask is made inert with a slow flow of nitrogen. A small sample was withdrawn by syringe and analyzed by FUR to establish the initial absorbance of the SiH vibration at 910 cm$^{-1}$. The temperature was then increased to 80° C. and the platinum catalyst was injected by syringe through the serum cap. An exotherm was observed and the temperature was maintained at 100° C. overnight (19 hours total reaction time), In Examples 7 and 8, 7 microliters COD (approx. 1:1 ratio of COD:Pt) were also added by syringe at 80° C. just prior to the catalyst injection.

Both the KOH test and analysis by FUR were done to determine whether SiH functional groups were still present in the reaction mixture at intervals and after overnight heating. At the end, hydrogen was generated when the KOH test was applied to the reaction mixtures of Comparative Examples 6 and 7. The FTIR spectrum of each sample also showed pronounced absorbance at 910 cm$^{-1}$ indicating that unreacted SiH was present. In contrast, the reaction mixtures of Examples 7 and 8 tested negatively for SiH in both analyses.

The reaction products were stripped of volatiles in vacuo and later characterized by $^{13}$C, $^{1}$H and $^{29}$Si NMR. $^{29}$Si NMR showed that conversion of SiH functionality in Comparative Example 7 was not only due to the desired reaction with the methallyl group (Si—C bond formation), but also to reaction with the terminal hydroxyl group (Si—O—C bond formation) of the polyether. Si—O—C bond formation was ~20 percent in the control (Comparative Example 7) and negligible in Example 8. Thus, use of COD as an additive was effective in completing the hydrosilylation of methyallyl polyethers and suppressing the formation of SiOC byproducts.

While the above description contains many specifics, these specifics should not be construed as limitations on the scope of the invention, but merely as exemplifications of preferred embodiments thereof. Those skilled in the art may envision many other possible variations that are within the scope and spirit of the invention as defined by the claims appended hereto.

Examples 9-44: General Procedure for Pilot Coater Formulation

A bucket was charged with 10 kg of SL6900, 600 g of SL6020D and 27 g of 3,5-dimethylhex-1-yn-3-ol (0.25 wt % S61 and Si—H/Si-vinyl 1.8/1). The formulation was mixed and split into 2 kg aliquots. To this 2 kg formulation, an aliquot of 1 wt % solution of COD in xylene was added. The Karstedt catalyst was added to the formulation right before the run and the material was mixed. The full formulation was run on the pilot coater. The coatings were analyzed by % extractables, coat weight, along with smear and migration tests. To determine the % extractables, a 100 cm$^2$ sample of a freshly coated and cured material was placed into an vial with 10 mL of solvent for 24 hours. The % extractables were determined by atomic absorption spectrophotometry. The % extractables for each run were performed in duplicate. The runs were conducted at 250° F. or 290° F. on Verso paper.

TABLE 3

Extractable data from the pilot coater run at a 30 ppm Pt loading of Karstedt's catalyst at various COD/Pt ratios at 250° F.

| COD equiv | Temp | Oven dwell time | Line speed | % Extractables |
|---|---|---|---|---|
| 0 | 250 | 4.5 | 200 | 17.8 |
| 0 | 250 | 3 | 300 | 23.2 |
| 0 | 250 | 1.5 | 600 | 39 |
| 1 | 250 | 4.5 | 200 | 5.6 |
| 1 | 250 | 3 | 300 | 9 |
| 1 | 250 | 1.5 | 600 | 27.2 |
| 2 | 250 | 4.5 | 200 | 4.1 |
| 2 | 250 | 3 | 300 | 9.5 |
| 2 | 250 | 1.5 | 600 | 18 |
| 3 | 250 | 4.5 | 200 | 9 |
| 3 | 250 | 3 | 300 | 8.6 |
| 3 | 250 | 1.5 | 600 | 23.2 |
| 5 | 250 | 4.5 | 200 | 12.9 |
| 5 | 250 | 3 | 300 | 18 |
| 5 | 250 | 1.5 | 600 | 28.7 |
| 100 | 250 | 4.5 | 200 | 8.7 |
| 100 | 250 | 3 | 300 | 15.3 |
| 100 | 250 | 1.5 | 600 | 32.6 |

Formulation contained SL6900/SL6020 (Si-h/Si-vinyl 1.8) and 0.25 wt % S61. The material was coated on SCK.

TABLE 4

Extractable data from the pilot coater run at a 10 ppm Pt loading of Karstedt's catalyst at various COD/Pt ratios at 290° F.

| COD equiv | Temp | Oven dwell time | Line speed | Extractables |
|---|---|---|---|---|
| 0 | 290 | 4.5 | 200 | 16.5 |
| 0 | 290 | 3 | 300 | 24.4 |
| 0 | 290 | 1.5 | 600 | 33.2 |
| 1 | 290 | 4.5 | 200 | 13.8 |
| 1 | 290 | 3 | 300 | 18 |
| 1 | 290 | 1.5 | 600 | 27.7 |
| 2 | 290 | 4.5 | 200 | 11.8 |
| 2 | 290 | 3 | 300 | 18 |
| 2 | 290 | 1.5 | 600 | 23.1 |
| 3 | 290 | 4.5 | 200 | 13.8 |
| 3 | 290 | 3 | 300 | 21.6 |
| 3 | 290 | 1.5 | 600 | 31.5 |
| 5 | 290 | 4.5 | 200 | 14.7 |
| 5 | 290 | 3 | 300 | 23.6 |
| 5 | 290 | 1.5 | 600 | 31.2 |
| 100 | 290 | 4.5 | 200 | 18.2 |
| 100 | 290 | 3 | 300 | 27.9 |
| 100 | 290 | 1.5 | 600 | 38.6 |

Formulation contained SL6900/SL6020 (Si-h/Si-vinyl 1.8) and 0.25 wt % S61. The material was coated on SCK.

TABLE 5

Extractable data from the pilot coater run at a 30 ppm Pt loading of Karstedt's catalyst at various COD/Pt ratios with low ECH loadings.

| COD equiv | Temp | Oven dwell time | Line speed | Extractables |
|---|---|---|---|---|
| 0 equiv COD | 250 | 4.5 | 200 | 6.9 |
| 0 equiv COD | 250 | 3 | 300 | 11.8 |
| 0 equiv COD | 250 | 1.5 | 600 | 15.9 |
| 0 equiv COD | 270 | 4.5 | 200 | 2.8 |
| 0 equiv COD | 270 | 3 | 300 | 3.8 |
| 0 equiv COD | 270 | 1.5 | 600 | 9 |
| 0 equiv COD | 290 | 4.5 | 200 | 1.9 |
| 0 equiv COD | 290 | 3 | 300 | 2 |
| 0 equiv COD | 290 | 1.5 | 600 | 4 |
| 1 equiv COD | 250 | 4.5 | 200 | 4.8 |

TABLE 5-continued

Extractable data from the pilot coater run at a 30 ppm Pt loading of Karstedt's catalyst at various COD/Pt ratios with low ECH loadings.

| COD equiv | Temp | Oven dwell time | Line speed | Extractables |
|---|---|---|---|---|
| 1 equiv COD | 250 | 3 | 300 | 7.7 |
| 1 equiv COD | 250 | 1.5 | 600 | 18.5 |
| 2 equiv COD | 250 | 4.5 | 200 | 5.4 |
| 2 equiv COD | 250 | 3 | 300 | 9 |
| 2 equiv COD | 250 | 1.5 | 600 | 12.8 |
| 2 equiv COD | 270 | 4.5 | 200 | 2.6 |
| 2 equiv COD | 270 | 3 | 300 | 2.3 |
| 2 equiv COD | 270 | 1.5 | 600 | 7 |
| 2 equiv COD | 290 | 4.5 | 200 | 1.9 |
| 2 equiv COD | 290 | 3 | 300 | 2 |
| 2 equiv COD | 290 | 1.5 | 600 | 4.5 |
| 3 equiv COD | 250 | 4.5 | 200 | 2.1 |
| 3 equiv COD | 250 | 3 | 300 | 3.5 |
| 3 equiv COD | 250 | 1.5 | 600 | 5.8 |
| 5 equiv COD | 250 | 4.5 | 200 | 7.1 |
| 5 equiv COD | 250 | 3 | 300 | 12.1 |
| 5 equiv COD | 250 | 1.5 | 600 | 16.1 |

Formulation contained SL6900/SL6020 (Si—H/Si-vinyl 1.8) and 0.07 wt % ECH. The material was coated on SCK.

While the above description contains many specifics, these specifics should not be construed as limitations on the scope of the invention, but merely as exemplifications of preferred embodiments thereof. Those skilled in the art may envision many other possible variations that are within the scope and spirit of the invention as defined by the claims appended hereto.

What is claimed is:

1. A composition comprising (a) a silyl hydride, (b) an alkenyl silicone compound, (c) a platinum compound, (d) a cyclodiene, and (e) optionally an inhibitor, where the cyclodiene (d) is a compound of the formula:

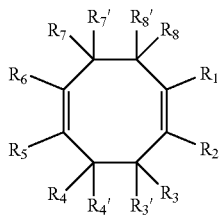

wherein $R^1$-$R^8$, $R^{3'}$, $R^{4'}$, $R^{7'}$, and $R^{8'}$ are independently hydrogen; an substituted or unsubstituted alkyl or aryl group optionally containing at least one heteroatom; an alkoxy; and a halogen radical; optionally $R^1$-$R^2$ and/or $R^5$-$R^6$ taken together may form a saturated or unsaturated ring structure, wherein the ratio of total moles of cyclodiene additive to moles of platinum is less than 2:1.

2. The composition of claim 1, wherein the diene comprises 1,5-cyclooctadiene; 1,5-dimethyl-1,5-cyclooctadiene; 1,6-dimethyl-1,5-cyclooctadiene, or a combination of two or more thereof.

3. The composition of claim 1, wherein the ratio of total moles of cyclodiene additive to moles of platinum is from less than 2:1 to about 0.1:1.

4. The composition of claim 1, wherein the platinum compound is a Pt(0) compound, and the ratio of total moles of cyclodiene additive to moles of platinum is from about 0.1:1 to about 100:1.

5. The composition of claim 1, wherein the platinum compound is chosen from Karstedt's catalyst, Ashby's catalyst, or a combination thereof.

6. The composition of claim 1, wherein the silylhydride is chosen from a compound of the formula $R^9{}_m SiH_p X_{4-(m+p)}$ and/or $M_a M^H{}_b D_c D^H{}_d T_e T^H{}_f Q_g$, where each $R^9$ is independently a substituted or unsubstituted aliphatic or aromatic hydrocarbyl group, X is alkoxy, acyloxy, halogen, or silazane, m is 1-3, p is 1-3 the subscripts a, b, c, d, e, f, and g are such that the molar mass of the silylhydride is between 100 and 100,000 Dalton; M represents a monofunctional group of formula $R^{10}{}_3 SiO_{1/2}$, a D represents a difunctional group of formula $R^{11}{}_2 SiO_{2/2}$, a T represents a trifunctional group of formula $R^{12} SiO_{3/2}$, Q represents a tetrafunctional group of formula $SiO_{4/2}$, $M^H$ represents $HR^{13}{}_2 SiO_{1/2}$, $T^H$ represents $HSiO_{3/2}$, and $D^H$ represents $R^{14} HSiO_{2/2}$; each occurrence of $R^{10-14}$ is independently C1-C18 alkyl, C1-C18 substituted alkyl, C6-C14 aryl or substituted aryl, wherein R10-14 optionally contains at least one heteroatom.

7. The composition of claim 1, wherein the alkenyl silicone comprises at least two unsaturated groups and has a viscosity of at least 50 cps at 25° C.

8. The composition of claim 1, wherein the alkenyl silicone is chosen from an compound of the formula:

$$M^{vi}{}_a T_b D_c M_d Q_e$$

wherein $M^{vi}{}_a = R^{31}{}_2 R^{32} SiO_{1/2}$; $T_b = R^{33} SiO_{3/2}$ where $R^{33}$ is chosen from $R^{31}$ or $R^{32}$; $D_c = R^{31} R^{33} SiO_{2/2}$ where $R^{33}$ is chosen from $R^{31}$ or $R^{32}$; $M_d = R^{31}{}_3 SiO_{1/2}$; and $Q_e = SiO_{4/2}$; $R^{31}$ is independently selected from a monovalent hydrocarbon radical having one to forty carbon, optionally containing at least one heteroatom; and $R^{32}$ is selected from a terminal olefinic monovalent hydrocarbon radical having two to forty carbon atoms, optionally containing at least one heteroatom; wherein the composition of the alkenyl silicone is such as to provide at least two unsaturated groups reactive to hydrosilylation per chain; a≥0, b≥0, d≥0, e≥0; and values for c such that the sum a+b+c+d+e is in the range 50-20,000.

9. The composition of claim 1, comprising a cure inhibitor (e) chosen from an ethylenically unsaturated amide, an aromatically unsaturated amide, an acetylenic compound, an ethylenically unsaturated isocyanate, an olefinic siloxane, an unsaturated hydrocarbon diester, an unsaturated hydrocarbon mono-ester of an unsaturated acid, an unsaturated anhydride, a conjugated ene-yne, a hydroperoxide, a ketone, a sulfoxide, an amine, a phosphine, a phosphite, a nitrite, a diaziridine, or a combination of two or more thereof.

10. The composition of claim 1, wherein the concentration of platinum is from about 100 parts per billion (ppb) to about 100 ppm.

11. The composition of claim 1, wherein component (e) is present in an amount of from about 0 to about 10 weight percent.

12. The composition of claim 1, wherein components (a)-(e) are provided in a single composition.

13. A coating formed from the composition of claim 12.

14. A substrate having a surface thereof at least partially coated with the coating of claim 13.

15. The substrate of claim 14, wherein the coating is anchored to the surface of the substrate.

16. A cured material prepared from the composition of claim 1.

17. The cured material of claim 16, wherein the cured material comprises component (d).

* * * * *